United States Patent [19]

Briles et al.

[11] Patent Number: 5,728,387
[45] Date of Patent: Mar. 17, 1998

[54] STRUCTURAL GENE OF PNEUMOCOCCAL PROTEIN

[75] Inventors: David E. Briles; Janet L. Yother, both of Birmingham, Ala.

[73] Assignee: University of Alabama at Birmingham Research Foundation, Birmingham, Ala.

[21] Appl. No.: 214,164

[22] Filed: Mar. 17, 1994

Related U.S. Application Data

[63] Continuation of Ser. No. 656,773, Feb. 15, 1991, abandoned.

[51] Int. Cl.$^6$ .......... A61K 39/02; A61K 39/09; C07K 1/00; C07K 14/00
[52] U.S. Cl. .......... 424/234.1; 530/350; 424/244.1
[58] Field of Search .......... 530/350; 424/244.1, 424/234.1

[56] References Cited

U.S. PATENT DOCUMENTS

| | | | |
|---|---|---|---|
| 4,496,538 | 1/1985 | Gordon | 424/92 |
| 4,673,574 | 6/1987 | Anderson | 424/92 |

OTHER PUBLICATIONS

McDaniel et al (I), J.Exp.Med. 160:386–397, 1984.
McDaniel et al (II), Microbial Pathogenesis 1:519–531, 1986.
McDaniel et al (III), J.Exp.Med. 165:381–394, 1987.
McDaniel et al (IV), Infect. Immun., 59:222–228, 1991.
Crain et al, Infect.Immun., 58:3293–3299, 1990.
Abstracts of 89th Annual Meeting of the American Society for Microbiology, p. 125, item D–257, May 1989.
Abstracts of 90th Annual Meeting of the American Society for Microbology, p. 98, item D–106, May 1990.
Abstracts of 3rd International ASM Conference on Streptococcal Genetics, p.11, item 12, Jun. 1990.
Talkington et al, Infect. Immun. 59:1285–1289, 1991.
Yother et al, J. Bacteriol. 174:601–609, 1992; and.
Yother et al, J. Bacteriol. 174:610–618, 1992.

*Primary Examiner*—Lynette F. Smith
*Attorney, Agent, or Firm*—Curtis Morris & Safford P.C.

[57] ABSTRACT

A purified pneumococcal surface protein A (PspA) comprises a truncated form of the PspA protein which is immunoprotective and contains the protective epitopes of PspA. The PspA protein is soluble in physiologic solution and lacks at least the cell membrane anchor region of the whole protein. The protein is formed by insertion-duplication of mutagenesis of *S. pneumoniae* with pspA gene and expression of the truncated protein into the growth medium.

9 Claims, 9 Drawing Sheets

|   | a | b | c | d | e | f | g |    |
|---|---|---|---|---|---|---|---|----|
| GLU | GLU | ser | pro | val | ala | ser |   |   |   |
|   | gln | ser | LYS | ala | GLU | LYS | ASP | 14 |
|   | tyr | ASP | ala | ala | LYS | LYS | ASP | 21 |
|   | ala | LYS | asn | ala | LYS | LYS | ala | 28 |
|   | val | GLU | ASP | ala | gln | LYS | ala | 35 |
|   | leu | ASP | ASP | ala | LYS | ala | ala | 42 |
|   | gln | LYS | LYS |   |   |   |   | 45 |

FIG. 2

```
pspa - sequence -> 1-phase Translation
DNA and derived amino acid 2086 b.p.
AAGCTTATGATA .... TCTTTAGGTACC  linear

1        /   1
AAG   CCT   ATG   ATA   TAG   AAA   TTT   GTA   ACA   AAA

31        /  11
ATG   TAA   TAT   AAA   ACA   CTT   GAC   AAA   TAT   TTA

61        /  21
CGG   AGG   AGG   CTT   ATA   CTT   AAT   ATA   AGT   ATA

91        /  31
GTC   TGA   AAA   TGA   CTA   TCA   GAA   AAG   AGG   TAA

121        /  41
ATT   TAG   ATG   AAT   AAG   AAA   AAA   ATG   ATT   TTA
            met   asn   lys   lys   lys   met   ile   leu
151        /  51
ACA   AGT   CTA   GCC   AGC   GTC   GCT   ATC   TTA   GGG
thr   ser   leu   ala   ser   val   ala   ile   leu   gly
181        /  61
GCT   GGT   TTT   GTT   GCG   TCT   CAG   CCT   ACT   GTT
ala   gly   phe   val   ala   ser   gln   pro   thr   val
211        /  71
GTA   AGA   GCA   GAA   GAA   TCT   CCC   GTA   GCC   AGT
val   arg   ala   glu   glu   ser   pro   val   ala   ser
241        /  81
CAG   TCT   AAA   GCT   GAG   AAA   GAC   TAT   GAT   GCA
gln   ser   lys   ala   glu   lys   asp   tyr   asp   ala
271        /  91
GCG   AAG   AAA   GAT   GCT   AAG   AAT   GCG   AAA   AAA
ala   lys   lys   asp   ala   lys   asn   ala   lys   lys
301        / 101
GCA   GTA   GAA   GAT   GCT   CAA   AAG   GCT   TTA   GAT
ala   val   glu   asp   ala   gln   lys   ala   leu   asp
```

*FIG. 3a*

| 331 | / | 111 | | | | | | | |
|---|---|---|---|---|---|---|---|---|---|
| GAT | GCA | AAA | GCT | GCT | CAG | AAA | AAA | TAT | GAC |
| asp | ala | lys | ala | ala | gln | lys | lys | tyr | asp |
| 361 | / | 121 | | | | | | | |
| GAG | GAT | CAG | AAG | AAA | ACT | GAG | GAG | AAA | GCC |
| glu | asp | gln | lys | lys | thr | glu | glu | lys | ala |
| 391 | / | 131 | | | | | | | |
| GCG | CTA | GAA | AAA | GCA | GCG | TCT | GAA | GAG | ATG |
| ala | leu | glu | lys | ala | ala | ser | glu | glu | met |
| 421 | / | 141 | | | | | | | |
| GAT | AAG | GCA | GTG | GCA | GCA | GTT | CAA | CAA | GCG |
| asp | lys | ala | val | ala | ala | val | gln | gln | ala |
| 451 | / | 151 | | | | | | | |
| TAT | CTA | GCC | TAT | CAA | CAA | GCT | ACA | CAC | AAA |
| tyr | leu | ala | tyr | gln | gln | ala | thr | asp | lys |
| 481 | / | 161 | | | | | | | |
| GCC | GCA | AAA | GAC | GCA | GCA | GAT | AAG | ATG | ATA |
| ala | ala | lys | asp | ala | ala | asp | lys | met | ile |
| 511 | / | 171 | | | | | | | |
| GAT | GAA | GCT | AAG | AAA | CGC | GAA | GAA | GAG | GCA |
| asp | glu | ala | lys | lys | arg | glu | glu | glu | ala |
| 541 | / | 181 | | | | | | | |
| AAA | ACT | AAA | TTT | AAT | ACT | GTT | CGA | GCA | ATG |
| lys | thr | lys | phe | asn | thr | val | arg | ala | met |
| 571 | / | 191 | | | | | | | |
| GTA | GTT | CCT | GAG | CCA | GAG | CAG | TTG | GCT | GAG |
| val | val | pro | glu | pro | glu | gln | leu | ala | glu |
| 601 | / | 201 | | | | | | | |
| ACT | AAG | AAA | AAA | TCA | GAA | GAA | GCT | AAA | CAA |
| thr | lys | lys | lys | ser | glu | glu | ala | lys | gln |

FIG. 3b

```
661         /    221
GAA  GCT  AAA  GCA  AAA  TTA  GAA  GAG  GCT  GAG
glu  ala  lys  ala  lys  leu  glu  glu  ala  glu
691         /    231
AAA  AAA  GCT  ACT  GAA  GCC  AAA  CAA  AAA  GTG
lys  lys  ala  thr  glu  ala  lys  gln  lys  val
721         /    241
GAT  GCT  GAA  GAA  GTC  GCT  CCT  CAA  GCT  AAA
asp  ala  glu  glu  val  ala  pro  gln  ala  lys
751         /    251
ATC  GCT  GAA  TTG  GAA  AAT  CAA  GTT  CAT  AGA
ile  ala  glu  leu  glu  asn  gln  val  his  arg
781         /    261
CTA  GAA  CAA  GAG  CTC  AAA  GAG  ATT  GAT  GAG
leu  glu  gln  glu  leu  lys  glu  ile  asp  glu
811         /    271
TCT  GAA  TCA  GAA  CAT  TAT  GCT  AAA  GAA  GGT
ser  glu  ser  glu  asp  tyr  ala  lys  glu  gly
841         /    281
TTC  CCT  GCT  CCT  CTT  CAA  TCT  AAA  TTG  GAT
phe  arg  ala  pro  leu  gln  ser  lys  leu  asp
871         /    291
GCG  AAA  AAA  GCT  AAA  CTA  TCA  AAA  CTT  GAA
ala  lys  lys  ala  lys  leu  ser  lys  leu  glu
901         /    301
CAG  TTA  AGT  GAT  AAG  ATT  GAT  GAG  TTA  GAC
gln  leu  ser  asp  lys  ile  asp  glu  leu  asp
931         /    311
GCT  GAA  ATT  GCA  AAA  CTT  GAA  GAT  CAA  CTT
ala  glu  ile  ala  lys  leu  glu  asp  gln  leu
961         /    321
AAA  GCT  GCT  GAA  GAA  AAC  AAT  AAT  GTA  GAA
lys  ala  ala  glu  glu  asn  asn  asn  val  glu
991         /    331
GAC  TAC  TTT  AAA  GAA  GGT  TTA  GAG  AAA  ACT
asp  tyr  phe  lys  glu  gly  leu  glu  lys  thr
```

*FIG. 3c*

| 1021 | / | 341 | | | | | | | |
|---|---|---|---|---|---|---|---|---|---|
| ATT | GCT | GCT | AAA | AAA | GCT | GAA | TTA | GAA | AAA |
| Ile | ala | ala | lys | lys | ala | glu | leu | glu | lys |
| 1051 | / | 351 | | | | | | | |
| ACT | GAA | GCT | GAC | CTT | AAG | AAA | GCA | GTT | AAT |
| thr | glu | ala | asp | leu | lys | lys | ala | val | asn |
| 1081 | / | 361 | | | | | | | |
| GAG | CCA | GAA | AAA | CCA | GCT | CCA | GCT | CCA | GAA |
| glu | pro | glu | lys | pro | ala | pro | ala | pro | glu |
| 1111 | / | 371 | | | | | | | |
| ACT | CCA | GCC | CCA | GAA | CCA | CCA | GCT | GAA | CAA |
| thr | pro | ala | pro | glu | ala | pro | ala | glu | gln |
| 1141 | / | 381 | | | | | | | |
| CCA | AAA | CCA | GCG | CCG | GCT | CCT | CAA | CCA | GCT |
| pro | lys | pro | ala | pro | ala | pro | gln | pro | ala |
| 1171 | / | 391 | | | | | | | |
| CCC | GCA | CCA | AAA | CCA | GAG | AAG | CCA | GCT | GAA |
| pro | ala | pro | lys | pro | glu | lys | pro | ala | glu |
| 1201 | / | 401 | | | | | | | |
| CAA | CCA | AAA | CCA | CAA | AAA | ACA | GAT | GAT | CAA |
| gln | pro | lys | pro | glu | lys | thr | asp | asp | gln |
| 1231 | / | 411 | | | | | | | |
| CAA | CCT | GAA | GAA | GAC | TAT | GCT | CGT | AGA | TCA |
| gln | ala | GLU | glu | asp | tyr | ala | arg | arg | ser |
| 1261 | / | 421 | | | | | | | |
| GAA | GAA | GAA | TAT | AAT | GGC | TTG | ACT | CAA | CAG |
| glu | glu | glu | tyr | asn | arg | leu | thr | gln | gln |
| 1291 | / | 431 | | | | | | | |
| CAA | CCG | CCA | AAA | CTT | CAA | AAA | CCA | GCT | CCT |
| gln | pro | pro | lys | ala | glu | lys | pro | ala | pro |
| 1321 | / | 441 | | | | | | | |
| GCA | CCA | CCA | ACA | GGC | TGG | AAA | CAA | GAA | AAC |
| ala | pro | lys | thr | gly | trp | lys | gln | glu | asn |
| 1351 | / | 451 | | | | | | | |
| GGT | ATG | TGG | TAC | TTC | TAC | AAT | ACT | GAT | GGT |
| gly | met | trp | tyr | phe | tyr | asn | thr | asp | gly |

*FIG. 3d*

| 1381 | / | 461 | | | | | | | |
|---|---|---|---|---|---|---|---|---|---|
| TCA | ATG | GCG | ACA | GGA | TGG | CTC | CAA | AAC | AAC |
| ser | met | ala | thr | gly | trp | leu | gln | asn | asn |
| 1411 | / | 471 | | | | | | | |
| GGT | TCA | TGG | TAC | TAC | CTC | AAC | AGC | AAT | GGT |
| gly | ser | trp | tyr | tyr | leu | asn | ser | asn | gly |
| 1441 | / | 481 | | | | | | | |
| GCT | ATG | GCT | ACA | GGT | TGG | CTC | CAA | TAC | AAT |
| ala | met | ala | thr | gly | trp | leu | gln | tyr | asn |
| 1471 | / | 491 | | | | | | | |
| GGT | TCA | TGG | TAT | TAC | CTC | AAC | GCT | AAC | GGC |
| gly | ser | trp | tyr | tyr | leu | asn | ala | asn | gly |
| 1501 | / | 501 | | | | | | | |
| GCT | ATG | GCA | ACA | GGT | TGG | GCT | AAA | GTC | AAC |
| ala | met | ala | thr | gly | trp | ala | lys | val | asn |
| 1531 | / | 511 | | | | | | | |
| GGT | TCA | TGG | TAC | TAC | CTC | AAC | GCT | AAT | GGT |
| gly | ser | trp | tyr | tyr | leu | asn | ala | asn | gly |
| 1561 | / | 521 | | | | | | | |
| GCT | ATG | GCT | ACA | GGT | TGG | CTC | CAA | TAC | AAC |
| ala | met | ala | thr | gly | trp | leu | gln | tyr | asn |
| 1591 | / | 531 | | | | | | | |
| GGT | TCA | TGG | TAT | TAC | CTC | AAC | GCT | AAC | GGC |
| gly | ser | trp | tyr | tyr | leu | asn | ala | asn | gly |
| 1621 | / | 541 | | | | | | | |
| GCT | ATG | GCA | ACA | GGT | TGG | GCT | AAA | GTC | AAC |
| ala | met | ala | thr | gly | trp | ala | lys | val | asn |
| 1651 | / | 551 | | | | | | | |
| GGT | TCA | TGG | TAC | TAC | CTC | AAC | GCT | AAT | GGT |
| gly | ser | trp | tyr | tyr | leu | asn | ala | asn | gly |
| 1681 | / | 561 | | | | | | | |
| GCT | ATG | GCT | ACA | GGT | TGG | CTC | CAA | TAC | AAC |
| ala | met | ala | thr | gly | trp | leu | gln | tyr | asn |
| 1711 | / | 571 | | | | | | | |
| GGT | TCA | TGG | TAC | TAC | CTC | AAC | GCT | AAC | GGT |
| gly | ser | trp | tyr | tyr | leu | asn | ala | asn | gly |

FIG. 3e

| 1741 | / | 581 | | | | | | | |
|---|---|---|---|---|---|---|---|---|---|
| GCT | ATG | GCT | ACA | GGT | TGG | GCT | AAA | GTC | AAC |
| ala | met | ala | thr | gly | trp | ala | lys | val | asn |
| 1771 | / | 591 | | | | | | | |
| GGT | TCA | TGG | TAC | TAC | CTC | AAC | GCT | AAT | GGT |
| gly | ser | trp | tyr | tyr | leu | asn | ala | asn | gly |
| 1801 | / | 601 | | | | | | | |
| GCT | ATG | GCA | ACA | GGT | TGG | GTG | AAA | GAT | GGA |
| ala | met | ala | thr | gly | trp | val | lys | asp | gly |
| 1831 | / | 611 | | | | | | | |
| GAT | ACC | TGG | TAC | TAT | CTT | GAA | GCA | TCA | GGT |
| asp | ser | trp | tyr | tyr | leu | glu | ala | ser | gly |
| 1861 | / | 621 | | | | | | | |
| GCT | ATG | AAA | GCA | AGC | CAA | TGG | TTC | AAA | GTA |
| ala | met | lys | ala | ser | gln | trp | phe | lys | val |
| 1891 | / | 631 | | | | | | | |
| TCA | GAT | AAA | TGG | TAC | TAT | GTC | AAT | GGT | TTA |
| ser | asp | lys | trp | tyr | tyr | val | asn | gly | leu |
| 1921 | / | 641 | | | | | | | |
| GCT | GCC | CTT | GCA | GTC | AAC | ACA | ACT | GTA | GAT |
| gly | ala | leu | ala | val | asn | thr | thr | val | asp |
| 1951 | / | 651 | | | | | | | |
| GGC | TAT | AAA | GTC | AAT | GCC | AAT | GGT | GAA | TGG |
| gly | tyr | lys | val | asn | ala | asn | gly | glu | trp |
| 1981 | / | 661 | | | | | | | |
| GTT | TAA | GCC | GAT | TAA | ATT | AAA | GCA | TGT | TAA |
| val | OCH | ala | asp | OCH | ile | lys | ala | cys | OCH |
| 2011 | / | 671 | | | | | | | |
| GAA | CAT | TTG | ACA | TTT | TAA | TTT | TGA | AAC | AAA |
| glu | his | leu | thr | phe | OCH | phe | OPA | asn | lys |
| 2041 | / | 681 | | | | | | | |
| GAT | AAG | CTT | CGA | TTG | AAT | AGA | TTT | ATG | TTC |
| asp | lys | val | arg | leu | asn | arg | phe | met | phe |
| 2071 | / | 691 | | | | | | | |
| GTA | TTC | TTT | AGG | TAC | | | | | |
| val | phe | phe | tyr | tyr | | | | | |

*FIG. 3f*

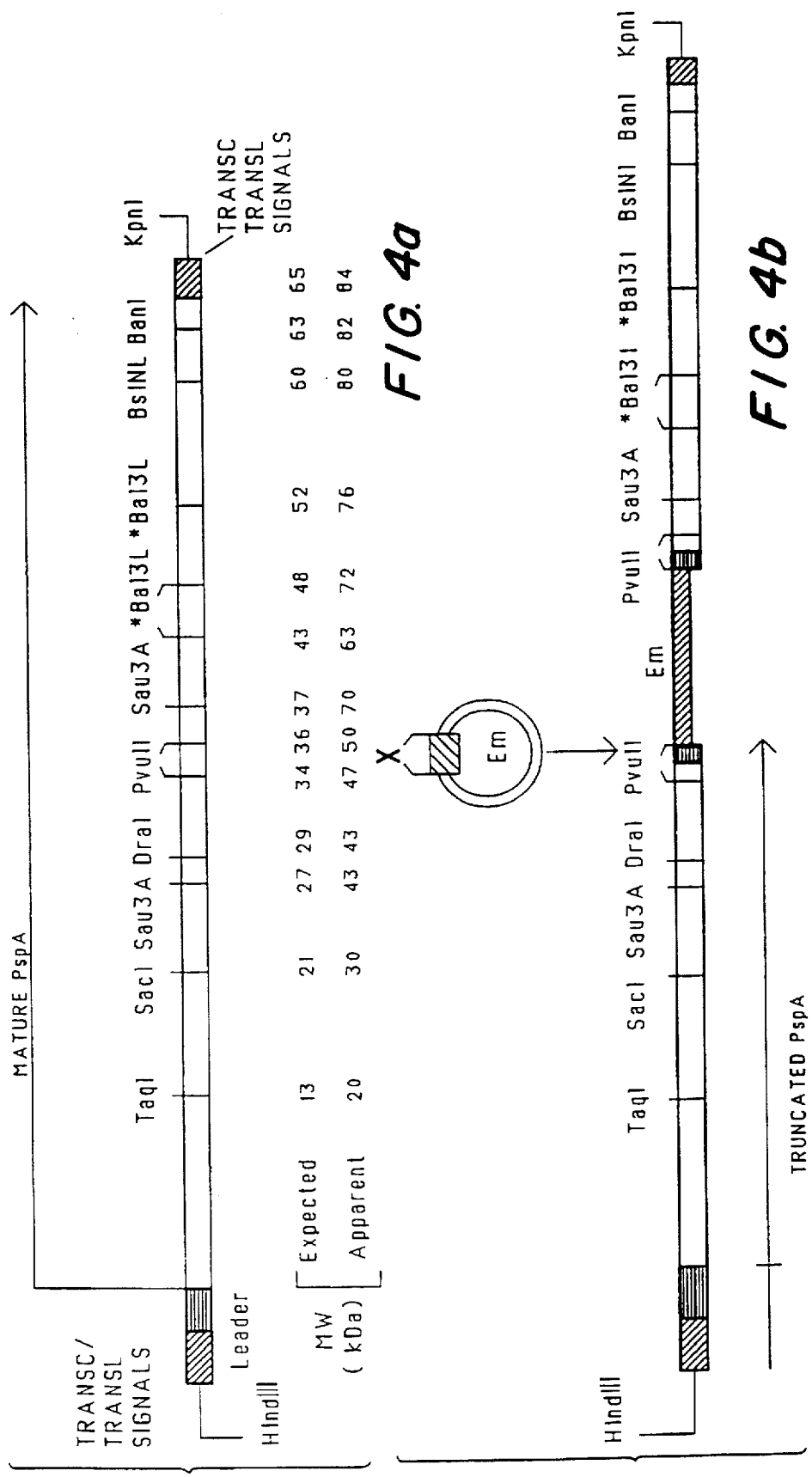

STRUCTURAL GENE OF PNEUMOCOCCAL PROTEIN

This application is continuation of application Ser. No. 07/656,773, filed Feb. 15, 1991, now abandoned.

FIELD OF INVENTION

The present invention is concerned with the development of an improved vaccine against pneumococcal infections.

BACKGROUND TO THE INVENTION

*Streptococcus pneumoniae* is an important cause of otitis media, meningitis, bacteremia and pneumonia. Despite the use of antibiotics and vaccines, the prevalence of pneumococcal infections has declined little over the last twenty-five years.

It is generally accepted that immunity to *Streptococcus pneumoniae* can be mediated by specific antibodies against the polysaccharide capsule of the pneumococcus. However, neonates and young children fail to make an immune response against polysaccharide antigens and can have repeated infections involving the same capsular serotype.

One approach to immunizing infants against a number of encapsulated bacteria is to conjugate the capsular polysaccharide antigens to protein to make them immunogenic. This approach has been successful, for example, with *Haemophilus influenzae b* (see U.S. Pat. No. 4,496,538 to Gordon and U.S. Pat. No. 4,673,574 to Anderson). However, there are over eighty known capsular serotypes of *S. pneumoniae* of which twenty-three account for most of the disease. For a pneumococcal polysaccharide-protein conjugate to be successful, the capsular types responsible for most pneumococcal infections would have to be made adequately immunogenic. This approach may be difficult, because the twenty-three polysaccharides included in the presently-available vaccine are not all highly immunogenic, even in adults.

An alternative approach to protecting children, and also the elderly, from pneumococcal infection would be to identify protein antigens that could elicit protective immune responses. Such proteins may serve as a vaccine by themselves, may be used in conjunction with successful polysaccharide-protein conjugates, or as carriers for polysaccharides.

In McDaniel et al (I), J. Exp. Med. 160:386–397, 1984, there is described the production of hybridoma antibodies that recognize cell surface polypeptide(s) on *S. pneumoniae* and protection of mice from infection with certain strains of encapsulated pneumococci by such antibodies. This surface protein antigen has been termed "pneumococcal surface protein A" or PspA for short.

In McDaniel et al (II), Microbial Pathogenesis 1:519–531, 1986, there are described studies on the characterization of the PspA. Considerable diversity in the PspA molecule in different strains was found, as were differences in the epitopes recognized by different antibodies.

In McDaniel et al (III), J. Exp. Med. 165:381–394, 1987, there is disclosed that immunization of X-linked immunodeficient (XID) mice with non-encapsulated pneumococci expressing PspA, but not isogenic pneumococci lacking PspA, protects mice from subsequent fatal infection with pneumococci.

In Crain et al, Infect. Immun., 56:3293–3299, 1990, there is described a rabbit antiserum that detects PspA in 100% (n=95) of clinical and laboratory isolates of strains of *S. pneumoniae*. When reacted with seven monoclonal antibodies to PspA, fifty-seven *S. pneumoniae* isolates exhibited thirty-one different patterns of reactivity.

The PspA protein type is independent of capsular type. It would seem that genetic mutation or exchange in the environment has allowed for the development of a large pool of strains which are highly diverse with respect to capsule, PspA, and possibly other molecules with variable structures. Variability of PspA's from different strains also is evident in their molecular weights, which range from 67 to 99 kD. The observed differences are stably inherited and are not the result of protein degradation.

Immunization with a partially purified PspA from a recombinant λ gt11 clone, elicited protection against challenge with several *S. pneumoniae* strains representing different capsular and PspA types, as described in McDaniel et al (IV), Infect. Immun. 59:222–228, 1991. Although clones expressing PspA were constructed according to that paper, the product was insoluble and isolation from cell fragments following lysis was not possible.

While the protein is variable in structure between different pneumococcal strains, numerous cross-reactions exist between all PspA's, suggesting that sufficient common epitopes may be present to allow a single PspA or at least a small number of PspA's to elicit protection against a large number of *S. pneumoniae* strains.

In addition to the published literature specifically referred to above, the inventors, in conjunction with co-workers, have published further details concerning PspA's, as follows:

1. Abstracts of 89th Annual Meeting of the American Society for Microbiology, p. 125, item D-257, May 1989;

2. Abstracts of 90th Annual Meeting of the American Society for Microbiology, p. 98, item D-106, May 1990; and 3. Abstracts of 3rd International ASM Conference on Streptococcal Genetics, p. 11, item 12, June 1990.

SUMMARY OF INVENTION

The present invention relates to the preparation of mutants of *S. pneumoniae* that secrete an immunogenic truncated form of the PspA protein, and isolation and purification of the secreted protein.

BRIEF DESCRIPTION OF DRAWINGS

FIG. 2 is the N-terminal amino acid sequence of PspA (SEQ ID No:3), wherein bold upper case letters denote charged hydrophilic amino acids, lower-case letters designate apolar, hydrophobic residues, and underlined bold lower case letters denote uncharged, polar, hydrophilic residues; and FIG. 3 is the DNA sequence of the pspA gene (SEQ ID No:1) with deduced amino acid sequence for the PspA protein (SEQ ID No:2); and FIG. 4 depicts the restriction map of pspA and the use of insertion-duplication mutagenesis to construct mutations in the pspA gene.

GENERAL DESCRIPTION OF INVENTION

Figure 1:
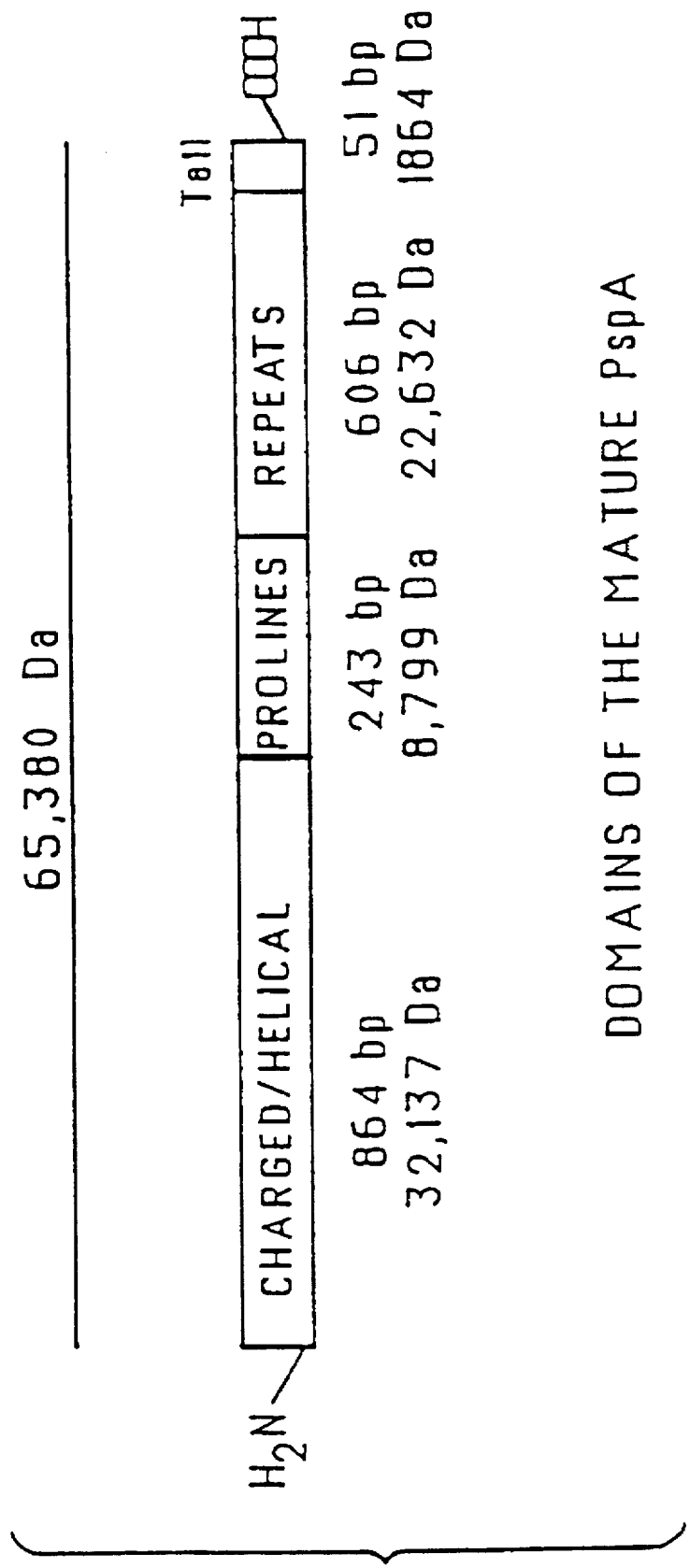
FIG. 1 is a schematic representation of the domains of the mature PspA.

According to one aspect of the present invention, there is provided a purified immunoprotective pneumococcal surface protein, comprising a truncated form of PspA which contains the immunoprotective epitopes of the protein and up to about 90% of the whole PspA protein and from which the cell membrane anchor region is absent.

Through the technique of insertion-duplication mutagenesis of the pspA gene of the strain Rx1 of *Streptococcus pneumoniae* with plasmids containing cloned fragments of the pspA structural gene, it has been possible to produce soluble fragments of PspA that are secreted by pneumococci.

In another aspect of the present invention, therefore, there is provided a method of forming an immunoprotective truncated PspA protein, which comprises effecting insertion-duplication mutagenesis of a bacterium with a pspA gene resulting in the coding of a truncated expressible PspA protein, growing the mutated bacterium to effect expression of a truncated PspA protein, and isolating the protein.

The molecular size of the purified truncated PspA protein obtained may be varied by directing the point of insertion, which determines the termination of gene expression, to different points in the pspA gene. For example, an N-terminal fragment of apparent molecular weight of 43 kD, constituting approximately one-half of the native protein, has been found useful.

The truncated segment which is produced by this procedure is capable of eliciting protection in mice from fatal challenge with type 3 *S. pneumoniae*, demonstrating for the first time that a purified PspA can elicit protection and that this portion of the protein contains protective epitopes of PspA.

Amino acid sequence information was obtained on the N-terminal 45 amino acids of the truncated segment of PspA. This sequence is shown in FIG. 2 (SEQ ID No:3). Predictive secondary structural analysis shows that this sequence has a very strong alpha-helical formation, with no non-helical inserts. About 51% of the segment is composed only of two amino acids, namely lysine, a charged amino acid, and alanine, a non-polar amino acid.

Analysis of this 45-amino acid sequence also reveals that it contains a seven-residue periodicity (see FIG. 2). In PspA, the periodicity begins with residue 8 and extends throughout the entire sequence, for nearly eleven turns of the helix. Positions "a" and "d" are occupied by apolar amino acids and position "b", "c" and "f" generally contain hydrophilic amino acids. Position "f" is predominantly occupied by lysine. Having regard to these observations, this region of PspA is very likely in an alpha-helical coiled-coil configuration.

We also have cloned and sequenced the entire coding region of pspA (see FIG. 3 SEQ ID No:1). The deduced amino acid sequence (SEQ ID No:2) reveals three distinct regions of the molecule, as seen in FIGS. 1 and 3. Accordingly, a further aspect of the present invention, there is provided a biologically-pure recombinant DNA molecule coding for the PspA protein and having the coding sequence set forth in FIG. 3 or having substantial homology thereto.

The amino terminal of the protein sequence, predicted from the DNA sequence, contains a 30 amino acid leader sequence and a 45 amino acid sequence identical to the 45 amino acid sequence of the N-terminal of PspA (FIG. 2). The amino end of the predicted protein sequence is highly charged and α-helical in nature. This region has homology with tropomyosin at the amino acid level (approximately 27% identity and 47% similarity). This homology is due largely to a repeating seven residue periodicity where the first and fourth amino acids are hydrophobic, the intervening amino acids are helix-promoting and the seventh amino acid is charged. This pattern is consistent with that of an α-helical coiled-coil molecule and indicates that the α-helical coil extends through the N-terminal half of the molecule.

Following the charged helical region is a proline-rich region in which 23 of 82 amino acids are prolines. Immediately carboxy to the proline-rich region is the first of ten highly homologous twenty amino acid repeats. The only significantly hydrophobic region in the sequenced portion of the molecule begins at the last repeat. This potential membrane-spanning region contains several charged amino acids preceding the translational stop codon.

The insertionally-inactivated mutants of *S. pneumoniae* lacking the C-terminal anchor regions are capable of growth in chemically-defined medium and secrete the N-terminal portion of the PspA protein into the medium. The N-terminal region of PspA is highly soluble in the culture medium and is much easier to isolate than the entire molecule. Soluble truncated molecules have been produced using insertional duplicational mutagenesis directed by the cloned PspA DNA fragments shown in FIG. 4. Expression of the same truncated construct (with the pneumococcal promoter) in *E.coli* results in the same PspA fragment being secreted into the periplasm of *E.coli*. PspA is readily released from the periplasm by hypotonic lysis.

Truncated PspA is isolated from culture medium of mutant pneumococci in any convenient manner, such as by tangential flow filtration. Ion-exchange chromatography then is performed on an anionic resin to purify the protein. In this procedure, the solution containing PspA is dialyzed to pH6 in 0.02 M salt solution and passed over the resin. The PspA is eluted from the resin with a gradient of 0.08 to 2.0 M ionic strength and is collected in the fraction between 0.34 and 0.87 M ionic strength, depending on the nature of the column used.

The PspA may be further purified by sodium dodecyl sulfate polyacrylamide gel (SDS-PAGE) electrophoresis. The PspA-containing portion of the gel is identified by staining of the gel and PspA is electroeluted from this portion.

The electrophoresis purification is convenient when only small qualities of PspA are being handled. As an alternative, more suited to large-scale production, the protein may be purified by size chromatography in a pH7 phosphate buffer.

Since it is possible to obtain expression of the truncated form of PspA into the culture medium, as opposed to it being trapped within the cell wall and making purification much more complicated, it should be possible to isolate other proteins that have been cloned into the truncated pspA gene by making fusion proteins between PspA and other proteins.

Another aspect of the present invention, therefore, provides a method for the production of cloned proteins which comprises fusing a pspA gene coding for a truncated form of PspA protein with the gene for another protein to form a fusion protein clone, transforming a bacterium with the fusion protein clone, growing the transformed bacterium to effect expression of a fusion protein comprising truncated PspA and the other protein into the culture medium, and isolating the fusion protein.

By using this technique, there can be produced cloned proteins in gram positive bacteria, such as pneumococci. This approach would overcome the problems inherent in the production of proteins in gram negative bacteria, such as *E. coli*, usually used for cloning, in particular, the need to purify the recombinant proteins from endotoxin and the toxicity of many gram positive DNA sequences in gram negative organisms.

As mentioned above, the truncated form of PspA provided herein contains the immunoprotective epitopes of the protein and hence is useful in a vaccine against pneunococcal infection. Accordingly, a yet further aspect of the present invention provides a vaccine against pneumococcal infection comprising, as the immunogenically-active component, the purified immunoprotective pneumococcal surface protein provided herein. Such vaccine also may contain immunoprotective polysaccharide-protein conjugates.

The truncated form of PspA also may be employed in conjugate with normally weakly-immunogenic or non-immunogenic molecules, such as various polysaccharides, to achieve immunogenic potentiation thereof. An additional aspect of the invention, therefore, provides a vaccine comprising, as the immunogenically-active component, a conjugate of the purified immunoprotective pneumococcal surface protein provided herein and a normally weakly-immunogenic or non-immunogenic molecule.

EXAMPLES

Example 1

This Example illustrates the preparation and growth of novel strains of S. pneumoniae.

The S. pneumoniae strain Rx1, which is a non-encapsulated derivative of capsular type 2 strain D39 (National Collection of Type Cultures, London, NCTC #7466), was subjected to insertional inactivation (as described in McDaniel et al (III) 1987, Crain et al 1990, Talkington et al 1991, in press, Infect. Immun.) with 10 different cloned fragments of PspA (see FIG. 4). These fragments have all been obtained from restriction digests of cloned-PspA DNA on a plasmid in strain E coli JY4313 (deposited with the American Type Culture Collection on Jan. 31, 1991 under ATCC accession number 68529). This insertional duplication mutagenesis (see FIG. 4) results in the termination of gene expression near the 5' end of the cloned fragment.

One of the resultant strains, JY2008 (deposited with the American Type Culture Collection on Jan. 24, 1991 under accession number 55143) which was produced by a fragment of DNA encoded in pKSD300 (McDaniel et al (III) 1987) produces a PspA fragment of 27 kDa (apparent molecular weight 43 kDa). This fragment is approximately 40% the size of the native 65 kDa (84 kDa apparent size) protein.

The expected molecular size is based on the deduced amino acid sequence and the apparent molecular size is based on migration in SDS-PAGE. The difference between expected and apparent molecular size is due to the conformation of the PspA fragment.

The proline and repeats/anchor regions (see FIG. 1) were deleted and the resulting protein was unable to attach to cell due to their absence. The unattached protein then could be isolated from culture supernatants, as described below.

By directing the insertion to different points in the pspA gene, different lengths of truncated, non-attached PspA protein derivatives can be produced.

The pneumococcal strain JY2008 was grown in 6 liters of a chemically defined medium (see Inf. Imm. 27:444) supplemented with 0.10% choline chloride, 0.075% L-cysteine hydrochloride and 0.25% $NaHCO_3$. The supernatant fluid of the mid-log phase culture of JY2008 was harvested using a 0.22 μm membrane tangential flow filter and concentrated 60 fold.

Introduction of the plasmid pKSD300 into the unmodified D39 strain similarly yielded the 43 kD truncated PspA protein. Introduction of the plasmid pKSD300 into the type 3 S. pneumoniae strain WU2 (PspA protein approximately 92 kD) yielded, upon growth of the organism, a non-attached truncated PspA protein of approximately 46 kD molecule size.

Example 2

This Example illustrates the purification of PspA.

The concentrated supernatant fluid, produced as described in Example 1, was washed in 0.1 M PBS, pH 7.2, and ultracentrifuged at 196,000×g. The supernatant fluid was diluted 1:5 in 20 mM L-histidine buffer-NaCl, the pH adjusted to 6.0 and then injected into a DEAE-fibered Isonet-D2 an ion exchange column.

A stepwise NaCl gradient from 80 mM to 2 M was applied to the column and PspA-containing fractions (0.32 to 0.64 M ionic strength) were pooled and separated on an SDA-polyacrylamide gel. The proteins on a representative section of the gel were stained with Conmassie Blue R-250 to identify PspA. The fraction containing PspA was excised from the remainder of the SDS-gel and electroeluted from the excised gel. The eluted protein was precipitated in a 50:50 methanol:acetone solvent and resuspended in PBS. Purity of product was confirmed by silver staining and Western Immunoblotting with mAb Xi126 (IgG 2b, k, see McDaniel et al (I), supra).

Example 3

This Example illustrates the isolation of PspA from the periplasmic space of Escherichia coli.

Isolation from the periplasmic space of E. coli was accomplished by standard techniques. E. coli strain JY4306 (which produces the 43 kDa N-terminal fragment of PspA, the amino acid sequence of which is shown in FIG. 3, and this strain was deposited with ATCC on Jan. 31, 1991 under accession number 68522) was washed in buffered saline, incubated in 20% sucrose, 10 mM EDTA, 25 mM Tris pH 7.7 for 10 minutes at 0° C. The cells then were were spun at 400×g for 10 minutes at 0° C. All supernatant was removed from the pellet and it was resuspended rapidly in about 100 volumes of 4° C. water. After 10 minutes the suspension was centrifuged at 4,000×g for 10 minutes at 4° C. The pellet was discarded and the supernatant, which contained the PspA was saved. Concentration of the supernatant was by standard procedures such as concentration against solid sucrose or ultrafiltration. Purification of the protein isolated from E. coli proceeded by the same chromatography techniques used for the isolated of the 43 kDa (truncated) PspA from the media of growing pneumococci.

Example 4

This Example illustrate the immunogenic properties of the PspA protein.

Sixteen 7-week old CBA/N mice carrying the Xid mutation (Jackson Laboratories, Bar Harber, Me.) were bled via the periorbital sinus to establish pre-exposure levels of antibody to PspA. Purified PspA, prepared as described in Example 2, was emulsified in complete Freund's adjuvant and injected subcutaneously into the inguinal and axillary regions, delivering approximately 5 μg of protein per mouse. Fourteen days later, the mice were injected intraperitoneally with 5 μg of PspA, prepared as described in Example 2. Control mice were immunized via the same routes with sterile SDS buffer. Seven days after the last immunization, all mice were bled via the periorbital sinus and were challenged intravenously with 300 CFU of the type 3 strain WU2, grown as described in Example 1.

Preimmunization and prechallenge sera were analyzed by Western immunoblots to establish baseline and postimmunization response to the truncated protein. The PspA of strain WU2 was electrophoresed and transferred to nitrocellulose membranes. The membranes were separated into strips and probed with the appropriate mouse antisera at a 1:50 dilution for 2 hours, incubated with biotinylated goat anti-mouse immunoglobulin for 1 hr, washed and incubated with Strepavidin-conjugated phosphatase. The membranes were developed with 5-bromo-4-chloro-3-indoyl phosphate toludine salt with 0.01% into blue tetrazolium.

Of the eight CBA/N mice immunized with the purified fragment of PspA, all were still alive 14 days after challenge with strain WU2 and none showed any signs of illness following challenge. Of the eight mice immunized with buffer controls, six were dead by two days post challenge, while the two remaining control mice appeared very sick, with ruffled fur, arched back and decreased movement, two to three days following challenge but survived. Chi-square analysis indicated that there was a significant difference (P<0.003) in survival between the immunized and control groups.

Preimmunization and prechallenge sera were analyzed by Western immunoblotting. None of the preimmunization sera contained antibody to truncated PspA. Postimmunization sera from eight of eight mice contained detectable antibodies to PspA, and six mice had very strong anti-PspA reactions. When the challenge strain WU2 was probed with the antisera, all the immunized mice had antibodies that were highly cross-reactive with the WU2 PspA epitopes. No control mice developed antibodies to PspA.

The immunization data is summarized in the following Table I:

TABLE I

| Immunogen | Detection of Antibody to PspA | Alive at 2 days post challenge | Alive at 14 days post challenge |
| --- | --- | --- | --- |
| Isolated PspA (Example 2) | 8/8 | 8/8 | 8/8 |
| Sterile SDS (control) | 0/8 | 2/8 | 2/8 |

As may be seen from the data in Table I, immunization with two 5 μg doses of the purified PspA molecule elicited protection against fatal infection of CBA/N mice and elicited antibodies reactive with the PspA of the challenge strain.

Example 5

This Example illustrates sequencing of the PspA protein.

Purified PspA, prepared as described in Example 2, was electrophoresed through 9% resolving gels containing recrystallized SDS with the Laemmli buffer system (Nature 227:680). The gels were soaked twice in a 10 mM 3-(cyclohexylamino)-1-propanesulfonic acid, pH 11.0, containing 10% methanol for 10 minutes. A polyvinylidene difluoride membrane (PVDF) was wetted completely for several seconds in 100% methanol, then washed in CAPS buffer for 10 min. PspA was electrotransferred to the PVDF membrane in CAPS buffer at 0.5 A for 1 hr. After transfer, the membrane was washed two times in deionized water for 5 min, and stained with 0.1% Coomassie Blue R-250 in 50% methanol for 20 minutes. The section of the membrane containing PspA was excised and destained in 40% methanol and 10% acetic acid for 5 min. The membrane was cut into small segments and stored in sterile Eppendorf tubes until sequencing.

The isolated PspA was sequenced directly from the PVDF membranes. FIG. 2 depicts the N-terminal 45 residue amino acid sequence. The DNA sequence of the whole pspA gene and the deduced amino acid sequence for the PspA protein are shown in FIG. 3.

SUMMARY OF DISCLOSURE

In summary of this disclosure, the present invention relates to a truncated PspA molecule capable of eliciting an immunoprotective response and hence containing the protective epitopes of PspA protein. Modifications are possible within the scope of this invention.

What we claim is:

1. An isolated and purified immunoprotective truncated pneumococcal surface protein A (PspA) containing immunoprotective epitopes of the PspA protein and up to 90% of the whole PspA protein and from which the cell membrane anchor region of the whole PspA protein is absent.

2. The protein of claim 1 containing approximately 50% of the whole PspA protein from which the cell membrane anchor region, the repeat region and the proline region are absent.

3. The protein of claim 1 comprising at least the N-terminal, protective epitope-containing region of the PspA protein.

4. The protein of claim 1 comprising at least the N-terminal, protective epitope-containing region of the PspA protein having the domains shown in FIG. 1.

5. The protein of claim 1 comprising an N-terminal α-helical coil region of the whole PspA protein.

6. The protein of claim 5 wherein said α-helical coil region has a seven residue periodicity.

7. The protein of claim 1 comprising the 43 kD N-terminal region of an 84 kD PspA protein.

8. A vaccine against pneumococcal infection, comprising, as the immunogenically-active component, the protein defined in claim 1, 2, 3, 4, 5, 6 or 7.

9. A vaccine, comprising, as the immunogenically-active component, a conjugate of the protein defined in claim 1, 2, 3, 4, 5, 6 or 7 and a normally weakly-immunogenic or non-immunogenic molecule.

* * * * *

UNITED STATES PATENT AND TRADEMARK OFFICE
CERTIFICATE OF CORRECTION

PATENT NO. : 5,728,387
DATED : March 17, 1998
INVENTOR(S) : Briles et al.

Page 1 of 5

It is certified that error appears in the above-identified patent and that said Letters Patent is hereby corrected as shown below:

In the Drawings delete Figure 3 and insert substitute Figure 3 (enclosed).

Signed and Sealed this

Twenty-sixth Day of February, 2002

*Attest:*

*Attesting Officer*

JAMES E. ROGAN
*Director of the United States Patent and Trademark Office*

FIG. 3A pspA - sequence -> 1-phase Translation
and derived amino acid
DNA λ sequence  2086 b.p.   AAGCTTATGATA ... TCTTTAGGTACC   linear

```
                                                                                                CONDENSUS-35
  1 /       1                   11           21          31           41             51
AAG CTT ATG ATA TAG AAA TTT GTA ACA AAA ATG TAA TAT AAA ACA CTT GAC AAA TAT TTA

61 /      21                                                                                   SD
CGG AGG AGG CTT AAT ATA AGT ATA GTC TCA CTA TCA GAA AAG AGG TAA

121 /      41  → START                                          -10
ATT TAG ATG AAT AAG AAA ATG ATT TTA ACA AGT CTA TAA GCC AGG GTC GCT ATC TTA
    met asn lys lys met ile leu thr ser leu ala ser val ala ile leu
                                LEADER 181 /      61
GCT GCT TTT GTT GCG TCT CAG CCT GTT GTA GAA GCA GAA TCT CCC GTA GCC AGT
ala ala phe val ala ser gln pro val val glu ala glu ser pro val ala ser 241 /      81                                                    91 /
GAG TCT AAA GCT GAG AAA GAC TAT GAT GCA GCG AAG AAA GAT GCT GCT AAG AAA AAA
glu ser lys ala glu lys asp tyr asp ala ala lys lys asp ala ala lys lys 301 /     101                                      111
GCA CTA GAA GAT GCT CAA AAG CTT TTA GAT GAT GCA GCA AAA AAG GCT CAG CAA TAT GAC
ala val glu asp ala gln lys leu leu asp asp ala ala lys lys ala gln gln tyr asp 361 /     121                                      131
GAC GAT CAG AAG AAA ACT GAG GAG CAA AAA ACT CGA GAA GCA GCT AAA AAG GCA AGA GCC ATC
ala asp gln lys lys thr glu glu gln lys thr arg glu ala ala lys lys ala arg ala 421 /     141                                      151
GAT AAG GCA GTG GCA GCA GCT GTT GCA CAA CAA CCT ACA GCA GTG ACA GAA GAC AAA
asp lys ala val ala ala ala val ala gln gln pro thr ala val thr glu asp lys
```

□=SIGNALS FOR TRANSCRIPTION/TRANSLATION.
ATG met = TRANSLATION START AT ATG

LEADER SEQUENCE IS CLEAVED.

"MATURE" PspA BEGINS WITH glu.

FIG. 3B

```
481 /  161
GCC GCA AAA GAC GCA GCA GAT AAG ATG ATA      GAT GAA GCT AAG CGC GAA GAG GCA
ala ala lys asp ala ala asp lys met ile      asp glu ala lys arg glu glu ala
                                    511 /                                171
                                    191
541 /  181
AAA ACT AAA TTT AAT ACT CTT CGA ATG GTA      GTT CCT GAG CAG CAG TTC GCT GAG
lys thr lys phe asn thr val arg met val      pro glu gln gln phe ala glu
                                    571 /
                                    191
601 /  201
AAG AAA AAA ATA TCA GAA GCA GCA CAA AAA      CCA CCA GAA CAG CTT ACT AAA
lys lys lys ile ser glu ala ala gln lys      pro pro glu gln leu thr lys
                                    631 /                                211
661 /  221
GAA GCT AAA GCA TTA GAA GAG GCT GAG AAA      GCT ACT GAA CTT AAA CTA GAA
glu ala lys ala leu glu glu ala glu lys      ala thr glu leu lys leu glu
                                    691 /                                231
721 /  241
GAT GCT GAA CTC GGT CCT CAA GCT AAA ATG      CCT GAT GCC AAA CAA AAA GTC
asp ala glu leu gly pro gln ala lys met      pro asp ala lys gln lys val
                                    751 /                                251
781 /  261
CTA CAA CAA GAG ATT GAT CAG TCT GAA ATC      GCT GAA AAT CAA GAA CAT AGA
leu gln gln glu ile asp gln ser glu ile      ala glu asn gln glu his arg
                                    811 /                                271
841 /  281
TTC CCT CCT CTT CAA TCT AAA TTG GAT CCC      AAA GCT ATA CTA TAT GAA GGT
phe pro pro leu gln ser lys leu asp pro      lys ala ile leu tyr glu gly
                                    871 /                                291
901 /  301
GAG TTA AGT GAT AAG AAG ATT GAT GAG GCT      GCA ATT GCA AAA CTT GAA CAA
glu leu ser asp lys lys ile asp glu ala      ala ile ala lys leu glu gln
                                    931 /                                311
961 /  321
AAA GCT GAA GAA AAC AAT GTA GAA GAC TAC      TTT AAA GAA GGT TTA GAG AAA
lys ala glu glu asn asn val glu asp tyr      phe lys glu gly leu glu lys
                                    991 /                                331
```

FIRST 45 aa, BEGINNING WITH glu, ARE SAME AS FOUND BY aa SEQUENCING (TALKINGTON ETC.)

α-HELICAL, CHARGED DOMAIN

FIG. 3C

```
1021 /         341
ATT GCT AAA AAA GCT GAA TTA GAA AAA GCT GAC CTT AAG AAA GCA GTT AAT
ile ala lys lys ala glu leu glu lys ala asp leu lys lys ala val asn
1081 /                   361
GAG CCA GAA AAA CCA GCT CCA GAA ACT CCA GCC CCA GAA GCA GCT GAA GAA
glu pro glu lys pro ala pro glu thr pro ala pro glu ala ala glu glu
1141 /                           381
CCA AAA CCA GCG CCG CCT CAA GCT CCC AAA GAG AAG CCA CCA GCT GAA
pro lys pro ala pro pro gln ala pro lys glu lys pro pro ala glu
                                  1171 /         391
CAA CCA AAA CCA GAA ACA CAA CAT CAA GAT CCC GCA GAA GAC TAT CCT GTT GAA
gln pro lys pro glu thr gln asp asp gln ala glu asp tyr ala arg ser
1201 /                                   411
CCA CCA GAA AAA CCA GAA ACA CAA CAT CAA GAT CCC GCA GAA GAC TAT CCT GTT GAA
pro lys pro glu thr gln asp asp gln ala glu asp tyr ala arg ser
1261 /                                           431
GAA GAA TAT AAT CGC TTG ACT CAA CAG CCA CCA AAA GCT GAA AAA CCA GCT CCT
glu glu tyr asn arg leu thr gln gln pro pro lys ala glu lys pro ala pro
1321 /                                                 451
GCA CCA AAA GGC TGG AAA CAA GAA AAC GGT TGG TAC TTC TAC AAT ACT GAT GGT
ala pro lys gly trp lys gln glu asn gly trp tyr phe tyr asn thr asp gly
1381 /                       471
TCA ATG GCG ACA GGA TGC CTC CAA AAC GGT TCA TGG TAC TAC CTC AAC AGC AAT GGT
ser met ala thr gly trp leu gln asn gly ser trp tyr tyr leu asn ser asn gly
1441 /                   491
GCT ATG GCT ACA GGT TGG CTT CAA AAC GGT TGG TAT TAC TTA CTC AAC AGC AAT GGT
ala met ala thr gly trp leu gln asn gly trp tyr tyr leu asn ser asn gly
1501 /               511
GCT ATG GCA ACA GGT TGG CTT CAA GTC AAC GGT TCA TGG TAC TAC CTC AAC AAC GGC
ala met ala thr gly trp leu lys val asn gly ser trp tyr tyr leu asn ala asn gly
1561 /           531
GCT ATG GCT ACA GGT TGG CTC CAA TAC AAC GGT TCA TAT TAT CTC AAC GCT AAC GGC
ala met ala thr gly trp leu gln tyr asn gly ser tyr tyr leu asn ala asn gly
                                                      } PROLINES
                                                      } PROLINE-
                                                        RICH
                                                        DOMAIN
```

FIG. 3D

```
1621 / 541
GCT ATG GCA ACA GGT TGG GCT AAA GTC AAC GGT TCA TAC TAC CTC AAC GCT AAT GGT
ala met ala thr gly trp ala lys val asn gly ser trp tyr leu asn ala asn gly
1681 / 561
GCT ATG GCT ACA GGT TGG CTC CAA TAC TAC CTC AAC GCT AAC GGT
ala met ala thr gly trp leu gln tyr tyr leu asn ala asn gly
                                        1771 / 591
GCT ATG GCT ACA GGT TGG GCT AAA GTC AAC GGT TCA TAC TAC CTC AAC GCT AAT GGT
ala met ala thr gly trp ala lys val asn gly ser trp tyr tyr leu asn ala asn gly
1801 / 601
GCT ATG GCA ACA GGT TGG GTC AAA GAT GGA AAC TGG TAC TAT CTT GAA AAC TCA GGT
ala met ala thr gly trp val lys asp gly asn trp tyr tyr leu glu asn ser gly
                                        1891 / 631
GCT ATG AAA GCA AGC CAA TGG TTC AAA TCA GAT AAA TGG TAC TAT AAA GCA TCA GGT
ala met lys ala ser gln trp phe lys ser asp lys trp tyr tyr lys ala ser gly
1921 / 641                              1951 / 651
GCT GCC CTT GCA GTC AAC ACA ACT GTA GAT GGC TAT AAA GTC AAT GCC GAA AAT GGT
ala ala leu ala val asn thr thr val asp gly tyr lys val asn ala glu asn gly
1981 /                                  2011 /
GTT GCC GAT TAA ATT AAA GCA TGT TAA GAA CAT TTC ACA TTT TAA GGT GAA TGG ]TAIL
val ala asp OCH ile lys ala cys OCH glu his leu thr phe OCH asn gly trp
2041 /                                  2071 / 691
val arg leu asn arg phe met phe val phe arg tyr lys
GAT AAG GTT CGA TTG AAT AGA TTT ATG TTC GTA TTC TTT AGG TAC
asp lys val arg leu asn arg phe met phe val phe arg tyr TAA                                              ]REPEAT
OCH                                               DOMAIN
TRANSLATION STOP (END) IS AT TAA OCH
```

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
      ( A ) LENGTH: 2085 base pairs
      ( B ) TYPE: nucleic acid
      ( C ) STRANDEDNESS: double
      ( D ) TOPOLOGY: linear ( i i ) MOLECULE TYPE: DNA (genomic)

( i x ) FEATURE:
      ( A ) NAME/KEY: intron
      ( B ) LOCATION: 1..1983

( i x ) FEATURE:

```
            ( A ) NAME/KEY: CDS
            ( B ) LOCATION: 127..1983

( x i ) SEQUENCE DESCRIPTION: SEQ ID NO:1:
```

| | | | |
|---|---|---|---|
| AAGCTTATGA TATAGAAATT TGTAACAAAA ATGTAATATA AAACACTTGA CAAATATTTA | | | 60 |
| CGGAGGAGGC TTATACTTAA TATAAGTATA GTCTGAAAAT GACTATCAGA AAAGAGGTAA | | | 120 |

```
ATTTAG ATG AAT AAG AAA AAA ATG ATT TTA ACA AGT CTA GCC AGC GTC                      168
       Met Asn Lys Lys Lys Met Ile Leu Thr Ser Leu Ala Ser Val
        1               5                   10

GCT ATC TTA GGG GCT GGT TTT GTT GCG TCT CAG CCT ACT GTT GTA AGA                     216
Ala Ile Leu Gly Ala Gly Phe Val Ala Ser Gln Pro Thr Val Val Arg
 15              20                  25                  30

GCA GAA GAA TCT CCC GTA GCC AGT CAG TCT AAA GCT GAG AAA GAC TAT                     264
Ala Glu Glu Ser Pro Val Ala Ser Gln Ser Lys Ala Glu Lys Asp Tyr
                 35                  40                  45

GAT GCA GCG AAG AAA GAT GCT AAG AAT GCG AAA AAA GCA GTA GAA GAT                     312
Asp Ala Ala Lys Lys Asp Ala Lys Asn Ala Lys Lys Ala Val Glu Asp
             50                  55                  60

GCT CAA AAG GCT TTA GAT GAT GCA AAA GCT GCT CAG AAA AAA TAT GAC                     360
Ala Gln Lys Ala Leu Asp Asp Ala Lys Ala Ala Gln Lys Lys Tyr Asp
         65                  70                  75

GAG GAT CAG AAG AAA ACT GAG GAG AAA GCC GCG CTA GAA AAA GCA GCG                     408
Glu Asp Gln Lys Lys Thr Glu Glu Lys Ala Ala Leu Glu Lys Ala Ala
     80                  85                  90

TCT GAA GAG ATG GAT AAG GCA GTG GCA GCA GTT CAA CAA GCG TAT CTA                     456
Ser Glu Glu Met Asp Lys Ala Val Ala Ala Val Gln Gln Ala Tyr Leu
 95                 100                 105                 110

GCC TAT CAA CAA GCT ACA GAC AAA GCC GCA AAA GAC GCA GCA GAT AAG                     504
Ala Tyr Gln Gln Ala Thr Asp Lys Ala Ala Lys Asp Ala Ala Asp Lys
                115                 120                 125

ATG ATA GAT GAA GCT AAG AAA CGC GAA GAA GAG GCA AAA ACT AAA TTT                     552
Met Ile Asp Glu Ala Lys Lys Arg Glu Glu Glu Ala Lys Thr Lys Phe
            130                 135                 140

AAT ACT GTT CGA GCA ATG GTA GTT CCT GAG CCA GAG CAG TTG GCT GAG                     600
Asn Thr Val Arg Ala Met Val Val Pro Glu Pro Glu Gln Leu Ala Glu
        145                 150                 155

ACT AAG AAA AAA TCA GAA GAA GCT AAA CAA AAA GCA CCA GAA CTT ACT                     648
Thr Lys Lys Lys Ser Glu Glu Ala Lys Gln Lys Ala Pro Glu Leu Thr
    160                 165                 170

AAA AAA CTA GAA GAA GCT AAA GCA AAA TTA GAA GAG GCT GAG AAA AAA                     696
Lys Lys Leu Glu Glu Ala Lys Ala Lys Leu Glu Glu Ala Glu Lys Lys
175                 180                 185                 190

GCT ACT GAA GCC AAA CAA AAA GTG GAT GCT GAA GAA GTC GCT CCT CAA                     744
Ala Thr Glu Ala Lys Gln Lys Val Asp Ala Glu Glu Val Ala Pro Gln
                195                 200                 205

GCT AAA ATC GCT GAA TTG GAA AAT CAA GTT CAT AGA CTA GAA CAA GAG                     792
Ala Lys Ile Ala Glu Leu Glu Asn Gln Val His Arg Leu Glu Gln Glu
            210                 215                 220

CTC AAA GAG ATT GAT GAG TCT GAA TCA GAA GAT TAT GCT AAA GAA GGT                     840
Leu Lys Glu Ile Asp Glu Ser Glu Ser Glu Asp Tyr Ala Lys Glu Gly
        225                 230                 235

TTC CGT GCT CCT CTT CAA TCT AAA TTG GAT GCC AAA AAA GCT AAA CTA                     888
Phe Arg Ala Pro Leu Gln Ser Lys Leu Asp Ala Lys Lys Ala Lys Leu
    240                 245                 250

TCA AAA CTT GAA GAG TTA AGT GAT AAG ATT GAT GAG TTA GAC GCT GAA                     936
Ser Lys Leu Glu Glu Leu Ser Asp Lys Ile Asp Glu Leu Asp Ala Glu
255                 260                 265                 270

ATT GCA AAA CTT GAA GAT CAA CTT AAA GCT GCT GAA GAA AAC AAT AAT                     984
Ile Ala Lys Leu Glu Asp Gln Leu Lys Ala Ala Glu Glu Asn Asn Asn
                275                 280                 285
```

```
GTA GAA GAC TAC TTT AAA GAA GGT TTA GAG AAA ACT ATT GCT GCT AAA       1032
Val Glu Asp Tyr Phe Lys Glu Gly Leu Glu Lys Thr Ile Ala Ala Lys
            290                 295                 300

AAA GCT GAA TTA GAA AAA ACT GAA GCT GAC CTT AAG AAA GCA GTT AAT       1080
Lys Ala Glu Leu Glu Lys Thr Glu Ala Asp Leu Lys Lys Ala Val Asn
        305                 310                 315

GAG CCA GAA AAA CCA GCT CCA GCT CCA GAA ACT CCA GCC CCA GAA GCA       1128
Glu Pro Glu Lys Pro Ala Pro Ala Pro Glu Thr Pro Ala Pro Glu Ala
    320                 325                 330

CCA GCT GAA CAA CCA AAA CCA GCG CCG GCT CCT CAA CCA GCT CCC GCA       1176
Pro Ala Glu Gln Pro Lys Pro Ala Pro Ala Pro Gln Pro Ala Pro Ala
335                 340                 345                 350

CCA AAA CCA GAG AAG CCA GCT GAA CAA CCA AAA CCA GAA AAA ACA GAT       1224
Pro Lys Pro Glu Lys Pro Ala Glu Gln Pro Lys Pro Glu Lys Thr Asp
                355                 360                 365

GAT CAA CAA GCT GAA GAA GAC TAT GCT CGT AGA TCA GAA GAA GAA TAT       1272
Asp Gln Gln Ala Glu Glu Asp Tyr Ala Arg Arg Ser Glu Glu Glu Tyr
            370                 375                 380

AAT CGC TTG ACT CAA CAG CAA CCG CCA AAA GCT GAA AAA CCA GCT CCT       1320
Asn Arg Leu Thr Gln Gln Gln Pro Pro Lys Ala Glu Lys Pro Ala Pro
        385                 390                 395

GCA CCA AAA ACA GGC TGG AAA CAA GAA AAC GGT ATG TGG TAC TTC TAC       1368
Ala Pro Lys Thr Gly Trp Lys Gln Glu Asn Gly Met Trp Tyr Phe Tyr
    400                 405                 410

AAT ACT GAT GGT TCA ATG GCG ACA GGA TGG CTC CAA AAC AAC GGT TCA       1416
Asn Thr Asp Gly Ser Met Ala Thr Gly Trp Leu Gln Asn Asn Gly Ser
415                 420                 425                 430

TGG TAC TAC CTC AAC AGC AAT GGT GCT ATG GCT ACA GGT TGG CTC CAA       1464
Trp Tyr Tyr Leu Asn Ser Asn Gly Ala Met Ala Thr Gly Trp Leu Gln
                435                 440                 445

TAC AAT GGT TCA TGG TAT TAC CTC AAC GCT AAC GGC GCT ATG GCA ACA       1512
Tyr Asn Gly Ser Trp Tyr Tyr Leu Asn Ala Asn Gly Ala Met Ala Thr
            450                 455                 460

GGT TGG GCT AAA GTC AAC GGT TCA TGG TAC TAC CTC AAC GCT AAT GGT       1560
Gly Trp Ala Lys Val Asn Gly Ser Trp Tyr Tyr Leu Asn Ala Asn Gly
        465                 470                 475

GCT ATG GCT ACA GGT TGG CTC CAA TAC AAC GGT TCA TGG TAT TAC CTC       1608
Ala Met Ala Thr Gly Trp Leu Gln Tyr Asn Gly Ser Trp Tyr Tyr Leu
    480                 485                 490

AAC GCT AAC GGC GCT ATG GCA ACA GGT TGG GCT AAA GTC AAC GGT TCA       1656
Asn Ala Asn Gly Ala Met Ala Thr Gly Trp Ala Lys Val Asn Gly Ser
495                 500                 505                 510

TGG TAC TAC CTC AAC GCT AAT GGT GCT ATG GCT ACA GGT TGG CTC CAA       1704
Trp Tyr Tyr Leu Asn Ala Asn Gly Ala Met Ala Thr Gly Trp Leu Gln
                515                 520                 525

TAC AAC GGT TCA TGG TAC TAC CTC AAC GCT AAC GGT GCT ATG GCT ACA       1752
Tyr Asn Gly Ser Trp Tyr Tyr Leu Asn Ala Asn Gly Ala Met Ala Thr
            530                 535                 540

GGT TGG GCT AAA GTC AAC GGT TCA TGG TAC TAC CTC AAC GCT AAT GGT       1800
Gly Trp Ala Lys Val Asn Gly Ser Trp Tyr Tyr Leu Asn Ala Asn Gly
        545                 550                 555

GCT ATG GCA ACA GGT TGG GTG AAA GAT GGA GAT ACC TGG TAC TAT CTT       1848
Ala Met Ala Thr Gly Trp Val Lys Asp Gly Asp Thr Trp Tyr Tyr Leu
    560                 565                 570

GAA GCA TCA GGT GCT ATG AAA GCA AGC CAA TGG TTC AAA GTA TCA GAT       1896
Glu Ala Ser Gly Ala Met Lys Ala Ser Gln Trp Phe Lys Val Ser Asp
575                 580                 585                 590

AAA TGG TAC TAT GTC AAT GGT TTA GGT GCC CTT GCA GTC AAC ACA ACT       1944
Lys Trp Tyr Tyr Val Asn Gly Leu Gly Ala Leu Ala Val Asn Thr Thr
                595                 600                 605
```

```
GTA GAT GGC TAT AAA GTC AAT GCC AAT GGT GAA TGG GTT TAAGCCGATT        1993
Val Asp Gly Tyr Lys Val Asn Ala Asn Gly Glu Trp Val
            610                 615

AAATTAAAGC ATGTTAAGAA CATTTGACAT TTTAATTTTG AAACAAAGAT AAGGTTCGAT     2053

TGAATAGATT TATGTTCGTA TTCTTTAGGT AC                                    2085
```

( 2 ) INFORMATION FOR SEQ ID NO:2:

( i ) SEQUENCE CHARACTERISTICS:
        ( A ) LENGTH: 619 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Lys Lys Lys Met Ile Leu Thr Ser Leu Ala Ser Val Ala Ile
 1               5                  10                  15

Leu Gly Ala Gly Phe Val Ala Ser Gln Pro Thr Val Val Arg Ala Glu
            20                  25                  30

Glu Ser Pro Val Ala Ser Gln Ser Lys Ala Glu Lys Asp Tyr Asp Ala
        35                  40                  45

Ala Lys Lys Asp Ala Lys Asn Ala Lys Lys Ala Val Glu Asp Ala Gln
    50                  55                  60

Lys Ala Leu Asp Asp Ala Lys Ala Ala Gln Lys Lys Tyr Asp Glu Asp
65                  70                  75                  80

Gln Lys Lys Thr Glu Glu Lys Ala Ala Leu Glu Lys Ala Ala Ser Glu
                85                  90                  95

Glu Met Asp Lys Ala Val Ala Ala Val Gln Gln Ala Tyr Leu Ala Tyr
            100                 105                 110

Gln Gln Ala Thr Asp Lys Ala Ala Lys Asp Ala Ala Asp Lys Met Ile
        115                 120                 125

Asp Glu Ala Lys Lys Arg Glu Glu Ala Lys Thr Lys Phe Asn Thr
    130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Ala Glu Lys Lys Ala Thr
            180                 185                 190

Glu Ala Lys Gln Lys Val Asp Ala Glu Glu Val Ala Pro Gln Ala Lys
        195                 200                 205

Ile Ala Glu Leu Glu Asn Gln Val His Arg Leu Glu Gln Glu Leu Lys
    210                 215                 220

Glu Ile Asp Glu Ser Glu Ser Glu Asp Tyr Ala Lys Glu Gly Phe Arg
225                 230                 235                 240

Ala Pro Leu Gln Ser Lys Leu Asp Ala Lys Lys Ala Lys Leu Ser Lys
                245                 250                 255

Leu Glu Glu Leu Ser Asp Lys Ile Asp Glu Leu Asp Ala Glu Ile Ala
            260                 265                 270

Lys Leu Glu Asp Gln Leu Lys Ala Ala Glu Glu Asn Asn Asn Val Glu
        275                 280                 285

Asp Tyr Phe Lys Glu Gly Leu Glu Lys Thr Ile Ala Ala Lys Lys Ala
    290                 295                 300

Glu Leu Glu Lys Thr Glu Ala Asp Leu Lys Lys Ala Val Asn Glu Pro
305                 310                 315                 320
```

```
Glu  Lys  Pro  Ala  Pro  Ala  Pro  Glu  Thr  Pro  Ala  Pro  Glu  Ala  Pro  Ala
               325                      330                      335

Glu  Gln  Pro  Lys  Pro  Ala  Pro  Ala  Pro  Gln  Pro  Ala  Pro  Ala  Pro  Lys
               340                      345                      350

Pro  Glu  Lys  Pro  Ala  Glu  Gln  Pro  Lys  Pro  Glu  Lys  Thr  Asp  Asp  Gln
               355                      360                      365

Gln  Ala  Glu  Glu  Asp  Tyr  Ala  Arg  Arg  Ser  Glu  Glu  Glu  Tyr  Asn  Arg
          370                      375                 380

Leu  Thr  Gln  Gln  Gln  Pro  Pro  Lys  Ala  Glu  Lys  Pro  Ala  Pro  Ala  Pro
385                      390                      395                      400

Lys  Thr  Gly  Trp  Lys  Gln  Glu  Asn  Gly  Met  Trp  Tyr  Phe  Tyr  Asn  Thr
               405                      410                      415

Asp  Gly  Ser  Met  Ala  Thr  Gly  Trp  Leu  Gln  Asn  Asn  Gly  Ser  Trp  Tyr
               420                      425                      430

Tyr  Leu  Asn  Ser  Asn  Gly  Ala  Met  Ala  Thr  Gly  Trp  Leu  Gln  Tyr  Asn
          435                      440                      445

Gly  Ser  Trp  Tyr  Tyr  Leu  Asn  Ala  Asn  Gly  Ala  Met  Ala  Thr  Gly  Trp
     450                      455                      460

Ala  Lys  Val  Asn  Gly  Ser  Trp  Tyr  Tyr  Leu  Asn  Ala  Asn  Gly  Ala  Met
465                      470                      475                      480

Ala  Thr  Gly  Trp  Leu  Gln  Tyr  Asn  Gly  Ser  Trp  Tyr  Tyr  Leu  Asn  Ala
               485                      490                      495

Asn  Gly  Ala  Met  Ala  Thr  Gly  Trp  Ala  Lys  Val  Asn  Gly  Ser  Trp  Tyr
               500                      505                      510

Tyr  Leu  Asn  Ala  Asn  Gly  Ala  Met  Ala  Thr  Gly  Trp  Leu  Gln  Tyr  Asn
          515                      520                      525

Gly  Ser  Trp  Tyr  Tyr  Leu  Asn  Ala  Asn  Gly  Ala  Met  Ala  Thr  Gly  Trp
     530                      535                      540

Ala  Lys  Val  Asn  Gly  Ser  Trp  Tyr  Tyr  Leu  Asn  Ala  Asn  Gly  Ala  Met
545                      550                      555                      560

Ala  Thr  Gly  Trp  Val  Lys  Asp  Gly  Asp  Thr  Trp  Tyr  Tyr  Leu  Glu  Ala
               565                      570                      575

Ser  Gly  Ala  Met  Lys  Ala  Ser  Gln  Trp  Phe  Lys  Val  Ser  Asp  Lys  Trp
               580                      585                      590

Tyr  Tyr  Val  Asn  Gly  Leu  Gly  Ala  Leu  Ala  Val  Asn  Thr  Thr  Val  Asp
          595                      600                      605

Gly  Tyr  Lys  Val  Asn  Ala  Asn  Gly  Glu  Trp  Val
     610                      615
```

( 2 ) INFORMATION FOR SEQ ID NO:3:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Glu  Glu  Ser  Pro  Val  Ala  Ser  Gln  Ser  Lys  Ala  Glu  Lys  Asp  Tyr  Asp
1                 5                      10                      15

Ala  Ala  Lys  Lys  Asp  Ala  Lys  Asn  Ala  Lys  Lys  Ala  Val  Glu  Asp  Ala
               20                      25                      30

Gln  Lys  Ala  Leu  Asp  Asp  Ala  Lys  Ala  Ala  Gln  Lys  Lys
               35                      40                      45
```